US00PP11179P

United States Patent [19]

Thomas

[11] Patent Number: Plant 11,179

[45] Date of Patent: Jan. 11, 2000

[54] CHRYSANTHEMUM PLANT NAMED 'YELLOW VOLARE'

[75] Inventor: Anthony David Thomas, Alajuela, Costa Rica

[73] Assignee: Yoder Brothers, Inc., Barberton, Ohio

[21] Appl. No.: 08/995,363

[22] Filed: Dec. 22, 1997

[51] Int. Cl.[7] ..... A01H 5/00

[52] U.S. Cl. ..... Plt./295

[58] Field of Search ..... Plt./82.2, 295

*Primary Examiner*—Howard J. Locker
*Attorney, Agent, or Firm*—C. A. Whealy

[57] ABSTRACT

A distinct cultivar of Chrysanthemum plant names Yellow Volare, characterized by its flat capitulum form; medium to large daisy-type inflorescences; attractive bright yellow ray florets and yellow disc florets; numerous inflorescences per plant; and good postproduction longevity.

1 Drawing Sheet

The present invention relates to a new and distinct cultivar of Chrysanthemum plant, botanically known as *Dendranthema grandiflora* and referred to by the cultivar name Yellow Volare.

The new cultivar was discovered by the inventor in September, 1996, in a controlled environment in Alajuela, Costa Rica, as a naturally-occurring mutation of the cut Chrysanthemum cultivar Volare (disclosed in U.S. Plant Pat. No. 8,058). The new cultivar was observed as a single plant within a population of flowering plants of the parent cultivar. The selection of this plant was based on its bright yellow ray floret color.

Asexual reproduction of the new cultivar by terminal cuttings taken at Alajuela, Costa Rica, has shown that the unique features of this new Chrysanthemum are stable and reproduced true to type in successive generations.

The following traits have been repeatedly observed and are determined to be the unique characteristics of Yellow Volare. These characteristics in combination distinguish Yellow Volare as a new and distinct cultivar:

1. Flat capitulum form.
2. Medium to large daisy-type inflorescences.
3. Bright yellow ray florets and yellow disc florets.
4. Numerous inflorescences per plant.
5. Good postproduction longevity with inflorescences maintaining good substance and color for more than three weeks in an interior environment.

The cultivar Yellow Volare has not been observed under all possible environmental conditions. The phenotype may vary somewhat with variations in environment such as temperature, daylength and light intensity, without, however, any variance in genotype.

Grown under similar cultural and environmental conditions, plants of the new Chrysanthemum are similar in plant habit to plants of the mutation parent, the cultivar Volare. Plants of the new Chrysanthemum and the cultivar Volare differ primarily in ray floret color. Additionally, plants of the cultivar Yellow Volare are usually about 10 to 15 cm taller, flower about two days earlier, and typically have inflorescences that are about 5 to 10 percent smaller than plants of the cultivar Volare.

BRIEF DESCRIPTION OF THE PHOTOGRAPHS

The accompanying colored photographs illustrate the overall appearance of the new cultivar, showing the colors as true as it is reasonably possible to obtain in colored reproduction of this type.

The photograph at the top of the sheet comprises a side perspective view of a typical flowering stem of Yellow Volare grown as a pinched cut Chrysanthemum.

The photograph at the bottom of the sheet comprises a close-up view of the lower (left) and upper (right) surfaces of a typical inflorescence of the cultivar Yellow Volare. Ray floret color appears darker than the actual color due to light reflectance.

DETAILED BOTANICAL DESCRIPTION

In the following description, color references are made to The Royal Horticultural Society Colour Chart except where general terms of ordinary dictionary significance are used. The following observations and measurements describe plants grown in Alajuela, Costa Rica, under commercial practice in a polyethylene-covered greenhouse with night temperatures ranging from 10 to 16° C. and day temperatures up to 30° C. After sticking unrooted cuttings of the new cultivar, plants received 5 weeks of long day/short nights following by short day/long nights until flowering. Measurements and numerical values represent averages for six typical pinched flowering stems.

Botanical classification: *Dendranthema grandiflora* cultivar Yellow Volare.

Commercial classification: Daisy spray-type cut Chrysanthemum.

Parentage: Naturally-occurring mutation of *Dendranthema grandiflora* cultivar Volare, disclosed in U.S. Plant Pat. No. 8,058.

Propagation:

*Type.*—Terminal tip cuttings.

*Time to rooting.*—7 to 10 days with soil temperatures of 21° C.

*Rooting habit.*—Fine, fibrous and well-branched.

Plant description:

*Appearance.*—Perennial herbaceous daisy spray-type cut flower. Stems upright, uniform habit and freely branching.

*Flowering plant height.*—About one meter under Costa Rican production conditions.

*Foliage description.*—Arrangement: Alternate. Length: About 10.5 cm. Width: About 5.5 cm. Apex: Acuminate to mucronate. Base: Attenuate. Margin: Palmately lobed. Texture: Upper and under surfaces slightly pubescent. Veins prominent on under surface. Color: Young foliage upper surface: 147A. Young foliage lower surface: 147B. Mature foliage upper surface: 147A. Mature foliage lower surface: 147B. Venation upper surface: 147B. Venation lower surface: 147B/147C. Petiole: Length: About 1.75 cm. Color: 147B/147C.

Flowering description:

*Appearance.*—Daisy inflorescence form. Inflorescences borne on terminals about foliage, arising from leaf axils. Disk and ray florets arranged acropetally on a flat capitulum.

*Flowering response.*—Under natural conditions, plant flowers in the autumn/winter in the Northern Hemisphere. At other times of the year, inflorescence initiation and development can be induced under short day/long night conditions (at least 13.5 hours of darkness). Plants exposed to long day/short night conditions after planting followed by photoinductive short day/long night conditions, flower about 56 days later.

*Postproduction longevity.*—In an interior environment, inflorescences of cut flowering stems will maintain good color and substance for at least three weeks in an interior environment.

*Quantity of inflorescences.*—About six inflorescences per flowering stem for pinched plants, more inflorescences per stem will develop on single-stem plants.

*Inflorescence size.*—Diameter: About 7 cm. Depth (height): About 1.25 cm. Diameter of disc: About 1.8 cm.

*Ray florets.*—Shape: Elongated, narrowly oblanceolate. Length: About 3.5 cm. Width: About 1 cm. Apex: Acute to tri-dentate. Base: Attenuate, fused at base. Margin: Entire. Texture: Satiny, smooth, glabrous. Aspect: Flat to somewhat cupped. Number of ray florets per inflorescence: About 55. Color: When opening, upper surface: 5A. When opening, lower surface: Close to 5C. Mature, upper surface: 5A. Mature, lower surface: 5D.

*Disc florets.*—Shape: Tubular. Length: About 8 mm. Width: Apex: About 1 mm. Base: About 2 mm. Number of disc florets per inflorescence: Numerous, about 210. Color: Immature: 154A or slightly darker. Mature: Apex: 12A. Mid-section: 154A or lighter. Base: White.

*Peduncle.*—Aspect: Strong and angled about 50° to the stem. Length: First peduncle: About 20 cm. Fourth peduncle: About 23.5 cm. Texture: Slightly pubescent. Color: 147B.

*Reproductive organs.*—Androecium: Present on disc florets only. Anther color: 14A. Pollen: Moderate, 14A in color. Gynoecium: Present on both ray and disc florets.

Disease resistance: Resistance to known Chrysanthemum diseases has not been observed on plants grown under commercial production conditions.

Seed production: Seed production has not been observed.

It is claimed:

1. A new and distinct cultivar of Chrysanthemum plant named Yellow Volare, as illustrated and described.

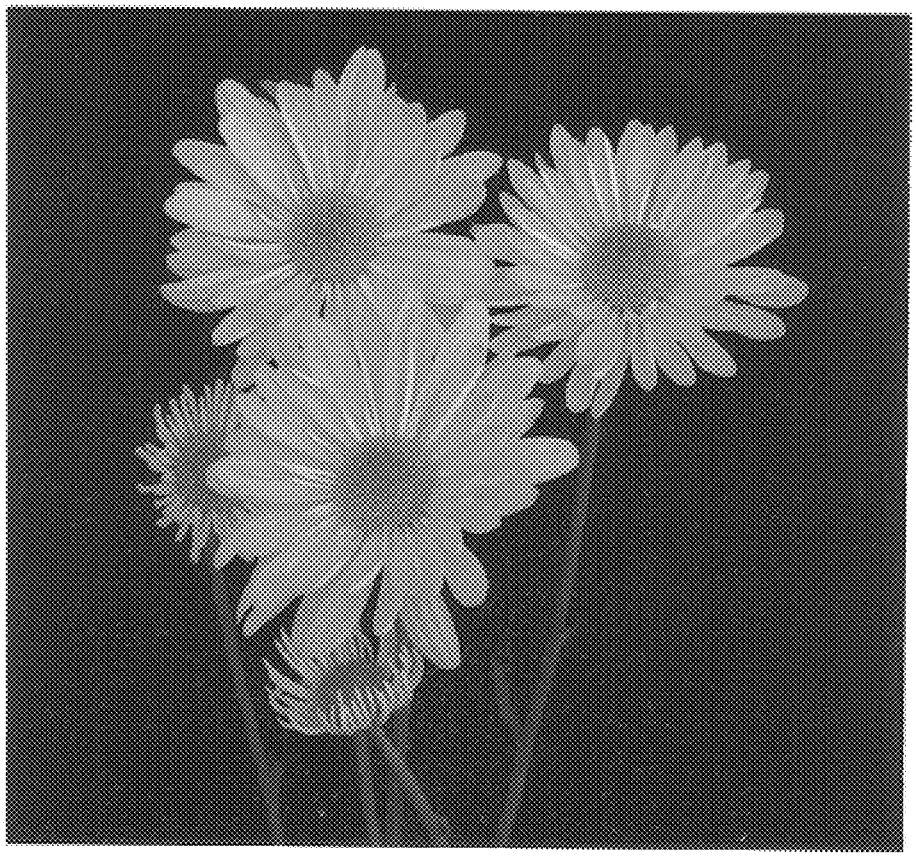
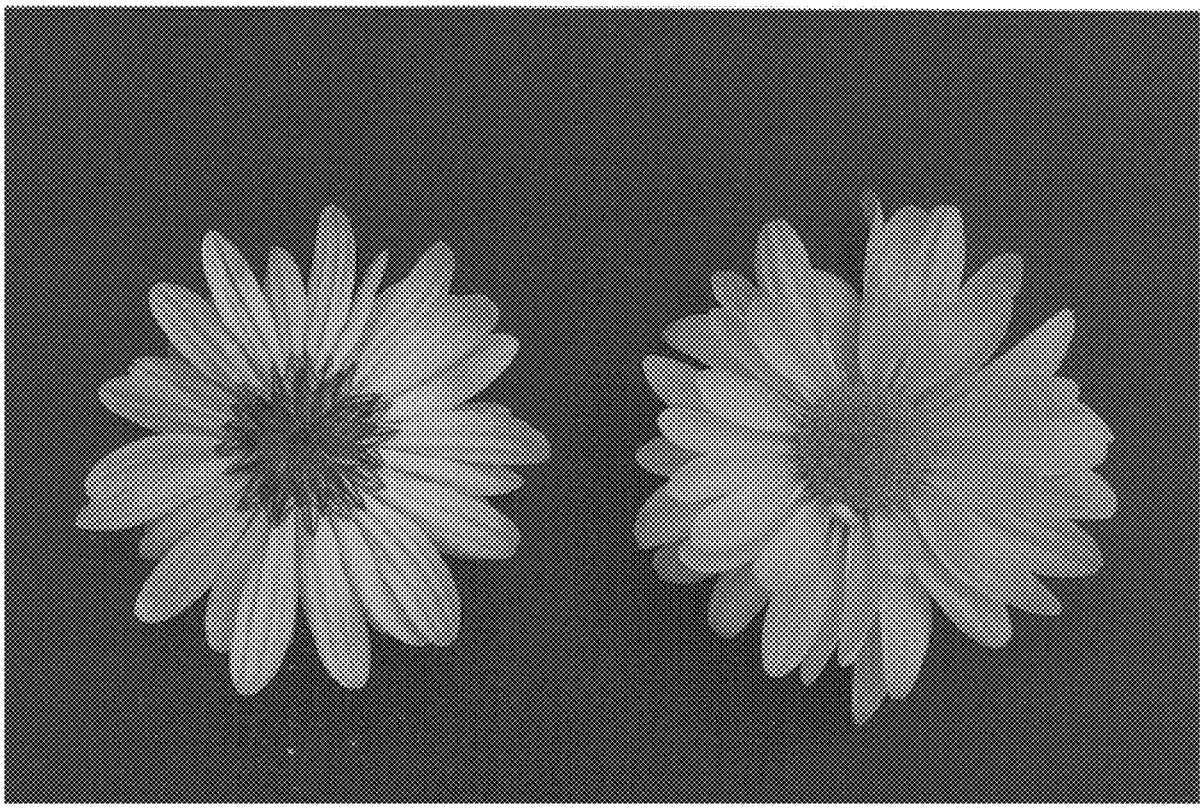

* * * * *